US012310279B2

(12) United States Patent
Schroeder et al.

(10) Patent No.: US 12,310,279 B2
(45) Date of Patent: May 27, 2025

(54) SYSTEM AND METHOD FOR AUTOMATICALLY CONTROLLING FERTILIZER APPLICATION WITHIN A FIELD

(71) Applicant: CNH Industrial Canada, Ltd., Saskatoon (CA)

(72) Inventors: Brittany Schroeder, Lowell, IN (US); Dennis George Thompson, Eagle Ridge (CA); Trevor Stanhope, Oak Lawn, IL (US)

( * ) Notice: Subject to any disclaimer, the term of this patent is extended or adjusted under 35 U.S.C. 154(b) by 390 days.

(21) Appl. No.: 17/843,316

(22) Filed: Jun. 17, 2022

(65) Prior Publication Data

US 2023/0403972 A1    Dec. 21, 2023

(51) Int. Cl.
*A01C 21/00* (2006.01)
*A01C 5/06* (2006.01)
(Continued)

(52) U.S. Cl.
CPC ............ *A01C 21/007* (2013.01); *A01C 5/062* (2013.01); *A01C 7/06* (2013.01); *A01C 7/08* (2013.01);
(Continued)

(58) Field of Classification Search
CPC ......... A01C 21/007; A01C 5/062; A01C 7/06; A01C 7/08; A01C 21/002; A01C 7/046;
(Continued)

(56) References Cited

U.S. PATENT DOCUMENTS 5,033,397 A    7/1991   Colburn, Jr.
6,393,927 B1   5/2002   Biggs et al.
(Continued)

FOREIGN PATENT DOCUMENTS

IN    2020/31036378    9/2021
WO    WO 1998/053312   11/1998
(Continued)

OTHER PUBLICATIONS

"Manure Constituent Sensing now available with John Deere HarvestLab™ 3000," John Deere, dated Jun. 11, 2019 (1 page) http://www.deere.com/en/news/all-news/2019june11-manure-constituent-sensing-now-available/.

(Continued)

*Primary Examiner* — Charles R Kasenge
(74) *Attorney, Agent, or Firm* — Rebecca Henkel; Peter K. Zacharias; Rickard K. DeMille

(57) ABSTRACT

A system for automatically controlling fertilizer application during the performance of a planting operation includes a row unit of a planting implement, the row unit being configured to deposit seeds within soil and having a fertilizer applicator configured to selectively dispense fertilizer. The system further includes a first sensor that generates first data indicative of a first nutrient-related parameter(s) within a (Continued)

field, and a second sensor supported on the planting implement that generates second data indicative of a second nutrient-related parameter(s) within the field, rearward of the row unit. A computing system determines an initial amount of the nutrient(s) within the field based on the first data, controls an operation of the fertilizer applicator to dispense the fertilizer onto the field, and determines an updated amount of the nutrient(s) within the field based on the second data.

19 Claims, 4 Drawing Sheets

(51) Int. Cl.
*A01C 7/06* (2006.01)
*A01C 7/08* (2006.01)
*G01N 33/24* (2006.01)

(52) U.S. Cl.
CPC ......... *A01C 21/002* (2013.01); *G01N 33/246* (2013.01); *G01N 33/245* (2024.05)

(58) Field of Classification Search
CPC ........... A01C 7/081; A01C 7/105; A01C 7/20; A01C 7/206; G01N 33/246; G01N 33/245
See application file for complete search history.

(56) References Cited

U.S. PATENT DOCUMENTS

| | | |
|---|---|---|
| 6,863,006 B2 | 3/2005 | Sandoval et al. |
| 8,451,449 B2 | 5/2013 | Holland |
| 10,080,323 B2 | 9/2018 | Lund et al. |
| 10,980,169 B2 | 4/2021 | Schoeny et al. |
| 11,064,646 B2 | 7/2021 | Zemenchik et al. |
| 2013/0008361 A1 | 1/2013 | Trevino et al. |
| 2021/0372983 A1 | 12/2021 | Zafar et al. |
| 2022/0232816 A1* | 7/2022 | Vandike ................ A01C 7/046 |

FOREIGN PATENT DOCUMENTS

| | | |
|---|---|---|
| WO | WO 2011/069563 | 6/2011 |
| WO | WO 2021/245202 | 12/2021 |

OTHER PUBLICATIONS

Schriber, "Smart Agriculture Sensors: Helping Small Farmers and positively Impacting Global Issues, Too," Sensor Technology, Mouser Electronics (2 pages) www.mouser.com/applications/smart-agricultural-sensors/.

* cited by examiner

SYSTEM AND METHOD FOR AUTOMATICALLY CONTROLLING FERTILIZER APPLICATION WITHIN A FIELD

FIELD OF THE INVENTION

The present disclosure relates generally to fertilizer application, such as fertilizer application performed using a planting implement, such as a planter or seeder, and, more particularly, to systems and methods for automatically controlling fertilizer application within a field during the performance of a planting operation within the field.

BACKGROUND OF THE INVENTION

Planting implements, such as planters, are generally known for performing planting operations within a field. A typical planter includes a plurality of row units, with each row unit including various ground engaging tools for creating a furrow within the soil, placing a seed within the furrow, and closing the soil around the seed. Fertilizer is preferably applied during the planting operation to ensure that nutrients are available for the early stages of plant growth and to prevent soil compaction from multiple passes. As such, planters may include fertilizer applicators configured to perform a fertilizer application during the planting operation, oftentimes according to a general application rate for the field or soil type. However, the nutrients already within the soil may vary throughout a field. As such, applying fertilizer at a constant application rate across a field may lead to areas of the field having nutrient levels exceeding allowable limits for the field or soil type, which may, in turn, exceed environmental standards.

Accordingly, an improved system and method for automatically controlling fertilizer application within a field would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a system for automatically controlling fertilizer application within a field during the performance of a planting operation. The system may include a row unit of a planting implement, with the row unit being configured to deposit seeds within soil. The row unit includes a furrow opening assembly configured to create a furrow in the soil for depositing seeds within a field. The row unit further includes a fertilizer applicator configured to selectively dispense fertilizer onto the field. The system may further include a first nutrient-related sensor configured to generate first data indicative of one or more first nutrient-related parameters within the field. Further, the system may include a second nutrient-related sensor supported on the planting implement, with the second nutrient-related sensor being configured to generate second data indicative of one or more second nutrient-related parameters within the field, rearward of the row unit relative to a direction of travel of the planting implement. Additionally, the system may include a computing system communicatively coupled to the fertilizer applicator. The computing system may be configured to receive the first data generated by the first nutrient-related sensor, determine an initial amount of each of the one or more nutrients within the field based at least in part on the first data, and control an operation of the fertilizer applicator to dispense the fertilizer onto the field. The computing system may further be configured to receive the second data generated by the second nutrient-related sensor, and to determine an updated amount of each of the one or more nutrients within the field based at least in part on the second data.

In another aspect, the present subject matter is directed to a method for automatically controlling fertilizer application within a field during the performance of a planting operation by a planting implement. The planting implement may include a row unit having a furrow opening assembly configured to create a furrow in soil for depositing seeds. The row unit may further have a fertilizer applicator configured to selectively dispense fertilizer onto the field. The method may include receiving, with a computing system, first data generated by a first nutrient-related sensor, with the first data being indicative of one or more first nutrient-related parameters within the field. The method may further include determining, with the computing system, an initial amount of each of the one or more nutrients within the field based at least in part on the first data and controlling, with the computing system, an operation of the fertilizer applicator to dispense the fertilizer onto the field. Moreover, the method may include receiving, with the computing system, second data generated by a second nutrient-related sensor supported on the planting implement, with the second data being indicative of one or more second nutrient-related parameters within the field, rearward of the row unit relative to a direction of travel of the planting implement. Additionally, the method may include determining, with the computing system, an updated amount of each of the one or more nutrients within the field based at least in part on the second data.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
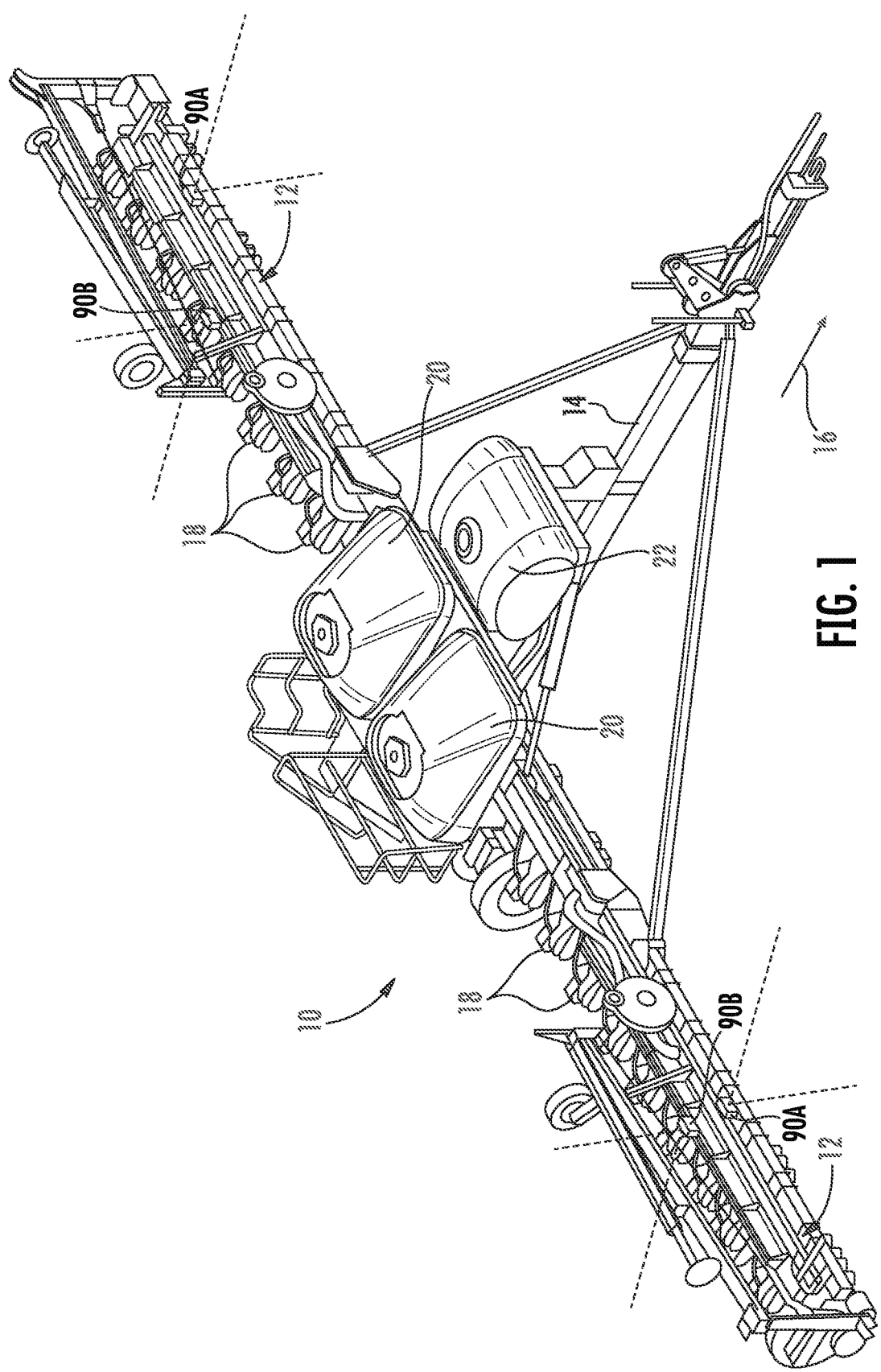
FIG. 1 illustrates a perspective view of one embodiment of a planting implement in accordance with aspects of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a further embodiment. Thus, it is intended that the present invention covers such modifications and variations as come within the scope of the appended claims and their equivalents.

In general, the present subject matter is directed to systems and methods for automatically controlling fertilizer application within a field during the performance of a planting operation. Specifically, in several embodiments, a planting implement may include a plurality of row units, with each row unit including various ground engaging tools for creating a furrow within the soil, placing a seed within the furrow, and closing the furrow around the seed. Each row unit may also include a fertilizer applicator controllable to selectively apply fertilizer adjacent to the furrow, between seeds in the furrow, and/or in any other suitable manner during the planting operation. In accordance with aspects of the present subject matter, the planting implement may also include, or be associated with, one or more forward-facing nutrient-related sensors configured to detect one or more nutrients within the field, before fertilizer is applied by the implement (e.g., forward of the planting implement relative to a direction of travel of the implement). Similarly, the planting implement may additionally include, or be associated with, one or more rearward-facing nutrient-related sensors configured to detect one or more nutrients within the field after fertilizer is applied by the implement (e.g., behind the planting implement relative to the direction of travel of the implement).

During a planting operation by the planting implement, a computing system may determine the initial amount of nutrient(s) within the field that the planting implement is about to pass over based on data generated by the forward-facing nutrient-related sensors. Thereafter, the computing system may control the operation of the fertilizer applicator(s) based on the nutrient(s) within the field. For instance, if the initial nutrient(s) within the field at a given location are too low compared to a corresponding threshold(s), and the fertilizer configured to be applied by the fertilizer will increase the nutrient(s), the computing system may control the operation of the fertilizer applicator(s) to apply the fertilizer within the field at the location indicated by the data from the forward-facing nutrient-related sensors. Conversely, if the initial nutrient(s) within the field at a given location are at or above the corresponding threshold(s), the computing system may control the operation of the fertilizer applicator(s) to not apply, or to stop applying, the fertilizer within the field at the location indicated by the data from the forward-facing nutrient-related sensors.

The computing system may then determine the new or updated amount(s) of the nutrient(s) within the field based on data from the rearward-facing nutrient-related sensors and determine the performance of the planting implement, specifically of the fertilizer applicator(s), based on the updated amount(s). For instance, if it is determined that the updated amount(s) of the nutrient(s) within the field is still too low compared to the associated threshold(s), the computing system may control the fertilizer applicator(s) to increase the flow and/or frequency of the dispensing of the fertilizer for subsequent areas within the field. Conversely, if it is determined that the nutrient(s) within the field are now too high compared to the associated threshold(s), the computing system may control the fertilizer applicator(s) to decrease the flow and/or frequency of the dispensing of the fertilizer for subsequent areas within the field. Additionally, if it is determined that the updated amount(s) of the nutrients is unchanged from the original amount of nutrient(s), the computing system may determine that the associated fertilizer dispenser(s) is impaired (e.g., plugged or is otherwise not functioning properly).

Accordingly, fertilizer application within a field during the performance of a planting operation with a planting implement may be automatically controlled based on real-time measurements of nutrients within the field by the planting implement to ensure that nutrients are available for the early stages of plant growth, while meeting environmental standards.

Referring now to the drawings, FIG. 1 illustrates a perspective view of one embodiment of a planting implement (e.g., a planter 10) in accordance with aspects of the present subject matter. As shown in FIG. 1, the planter 10 may include a laterally extending toolbar or frame assembly 12 connected at its middle to a forwardly extending tow bar 14 to allow the planter 10 to be towed by a work vehicle (not shown), such as an agricultural tractor, in a direction of travel (e.g., as indicated by arrow 16). The frame assembly 12 may generally be configured to support a plurality of seed planting units (or row units) 18. As is generally understood, each row unit 18 may be configured to deposit seeds at a desired depth beneath the soil surface and at a desired seed spacing as the planter 10 is being towed by the work vehicle, thereby establishing rows of planted seeds. In some embodiments, the bulk of the seeds to be planted may be stored in one or more hoppers or seed tanks 20. Thus, as seeds are planted by the row units 18, a pneumatic distribution system may distribute additional seeds from the seed tanks 20 to the individual row units 18 via one or more delivery lines 21. Additionally, one or more tanks 22 may store agricultural products, such as insecticides, herbicides, fungicides, fertilizers, and/or the like.

It should be appreciated that, for purposes of illustration, only a portion of the row units 18 of the planter 10 have been shown in FIG. 1. In general, the planter 10 may include any number of row units 18, such as 6, 8, 12, 16, 24, 32, or 36 row units. In addition, it should be appreciated that the lateral spacing between row units 18 may be selected based on the type of crop being planted. For example, the row units 18 may be spaced approximately 20 or 30 inches from one another for planting corn, and approximately 15 inches from one another for planting soybeans.

It should also be appreciated that the configuration of the planter 10 described above and shown in FIG. 1 is provided only to place the present subject matter in an exemplary field of use. Thus, it should be appreciated that the present subject matter may be readily adaptable to any manner of planter configuration or any other planting implement configuration, including seeders.

Figure 2:
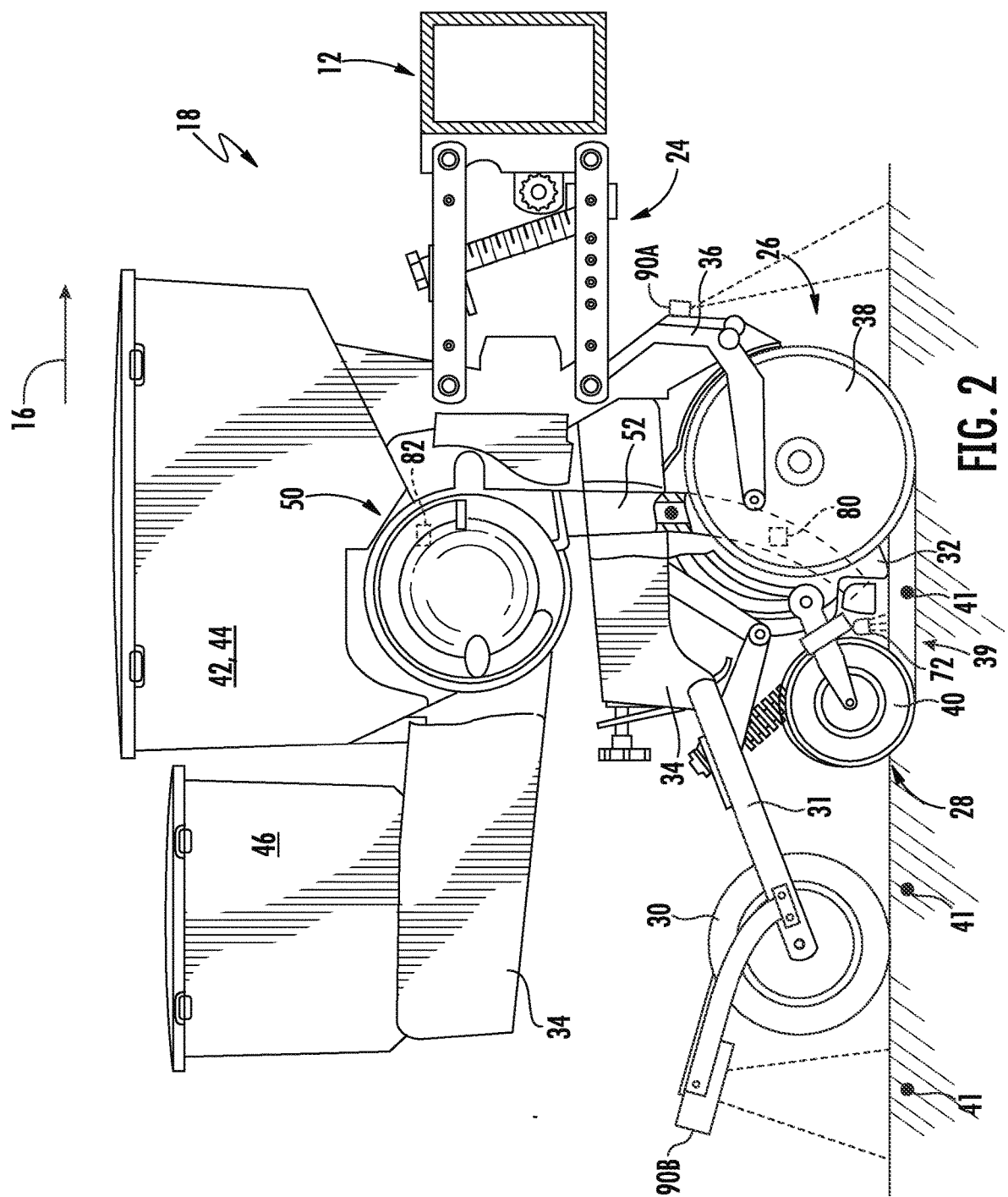
FIG. 2 illustrates a side view of one embodiment of a row unit suitable for use with a planting implement in accordance with aspects of the present subject matter.

Referring now to FIG. 2, a side view of one embodiment of a row unit 18 is illustrated in accordance with aspects of the present subject matter. As shown, the row unit 18 includes a linkage assembly 24 configured to mount the row unit 18 to the toolbar or frame assembly 12 of the planter 10. As shown in FIG. 2, the row unit 18 also includes a furrow opening assembly 26, a furrow closing assembly 28, and a press wheel 30. In general, the furrow opening assembly 26 may include a gauge wheel (not shown) operatively connected to a frame 34 of the row unit 18 via a support arm 36. Additionally, the opening assembly 26 may also include one or more opening disks 38 configured to excavate a trench or furrow 39 in the soil, and a firming point 32. The gauge wheel is not shown to better illustrate the opening disk 38. As is generally understood, the gauge wheel may be configured to engage the surface of the field, with the height of the opening disk(s) 38 being adjusted with respect to the position of the gauge wheel to set the desired depth of the furrow 39 being excavated. Moreover, as shown, the furrow closing assembly 28 may include a closing disk(s) 40 configured to close the furrow 39 after seeds 41 have been deposited therein. The press wheel 30 may then be configured to roll over the closed furrow 39 to firm the soil over the seed 41 and promote favorable seed-to-soil contact.

Additionally, as shown in FIG. 2, the row unit 18 may include one or more seed hoppers 42, 44 and a tank 46 supported on the frame 34. In general, the seed hopper(s) 42, 44 may be configured to store seeds 41 received from the seed tanks 20, which are to be deposited within the furrow 39 as the row unit 18 moves over and across the field. For instance, in several embodiments, the row unit 18 may include a first seed hopper 42 configured to store seeds of a first seed type and a second hopper 44 configured to store seeds of a second seed type. However, both seed hoppers 42, 44 may be configured to store the same type of seeds. Furthermore, the tank 46 may be configured to store fluid or granular fertilizer received from the tank 22 (FIG. 1), which is to be applied near the seeds dispensed from the seed hoppers 42, 44, or insecticide.

Moreover, the row unit 18 may include a seed meter 50 provided in operative association with the seed hopper(s) 42, 44. In general, the seed meter 50 may be configured to uniformly release seeds 41 received from the seed hopper(s) 42, 44 for deposit within the furrow 39. For instance, in one embodiment, the seed meter may be coupled to a suitable vacuum source (e.g., a blower powered by a motor and associated tubing or hoses) configured to generate a vacuum or negative pressure that attaches the seeds to a rotating seed disk of the seed meter 50, which controls the rate at which the seeds 41 are output from the seed meter 50 to an associated seed tube 52. As shown in FIG. 2, the seed tube 52 may extend vertically from the seed meter 50 toward the ground to facilitate delivery of the seeds 41 output from the seed meter 50 to the furrow 39.

The row units 18 may further include a fertilizer applicator 72 supported thereon and configured to spray or otherwise dispense the fertilizer (e.g., from the tank(s) 22, 46) near the seeds 41 dispensed from the row units 18 as the seeds 41 are dispensed from the row units 18 or after the seeds 41 are deposited in the furrow 39. For example, as shown in FIG. 2, the fertilizer applicator 72 may be mounted on the row unit 18 such that the fertilizer applicator 72 is positioned to spray the fertilizer between the opening disk 38 and the closing disk 40 onto the field next to the furrow 39 proximate the seeds 41. The fertilizer applicator 72 may comprise any suitable elements to provide the fertilizer, such as a pump, a conduit, a valve and/or the like.

In several embodiments, the row unit 18 may also include one or more sensors 80, 82 for generating data indicative of the timing and/or frequency of seeds 41 being deposited into the furrow 39 between the opening and closing assemblies 26, 28. For instance, as shown in the illustrated embodiment, the row unit 18 may include one or more seed tube sensors 80 configured to detect seeds as they fall or otherwise travel through the seed tube 52. In such an embodiment, the seed tube sensor 80 may generally correspond to any suitable sensor or sensing device configured to detect seeds passing through the seed tube 52 (e.g., whether falling through the tube 52 via gravity or by being conveyed through the tube 52 via a driven belt or other seed-transport means extending within the seed tube 52). For example, the seed tube sensor 80 may correspond to an optical sensor (e.g., a break-beam sensor or a reflectance sensor), a microwave sensor, a Hall-effect sensor, and/or the like.

In addition to the seed tube sensor 80 (or as an alternative thereto), the row unit 18 may include other sensors for generating data indicative of the timing and frequency of seeds 41 being deposited into the furrow 39. For instance, as shown in the illustrated embodiment, the row unit 18 may include one or more seed meter sensors 82 configured to detect seeds 41 that are being or will be discharged from the seed meter 50. Specifically, in one embodiment, the seed meter sensor(s) 82 may correspond to a post-singulation sensor positioned within the seed meter 50 such that the sensor's detection zone is aligned with a location within a post-singulation region of the seed meter 50: (1) across which the seed disc or other seed transport member is rotated following the singulator (not shown) of the seed meter 50; and/or (2) through which each seed 41 to be discharged from seed meter 50 passes following release of the seed 41 from the seed disc. In such an embodiment, the seed meter sensor 82 may generally correspond to any suitable sensor or sensing device configured to detect seeds that are being or will be discharged from the seed meter 50. For example, the seed meter sensor 82 may correspond to an optical sensor (e.g., a break-beam sensor or a reflectance sensor), a microwave sensor, a Hall-effect sensor, and/or the like.

As will be described below in greater detail, it may be beneficial to control the fertilizer applicator 72 based on the actual amounts of nutrients present within the soil of the field at the time of the planting operation instead of based on a field map of the nutrients present generated during a previous agricultural operation or generally based on the type of soil and/or the type of seed to be planted. Thus, in accordance with aspects of the present subject matter, sensors 90A, 90B may be used to generate data indicative of nutrients within the field at the time of the planting operation. For instance, the planting implement 10 may include one or more forward nutrient-related sensors 90A configured to generate data indicative of one or more nutrient-related parameters within the field, forward of the planting implement 10 relative to the direction of travel 16, before fertilizer has been dispensed by the fertilizer applicator(s) 72. Additionally, the planting implement 10 may include one or more rearward nutrient-related sensors 90B configured to generate data indicative of one or more nutrient-related parameters within the field behind the planting implement 10 relative to the direction of travel 16, after being worked by the planting implement 10, particularly after any fertilizer would have been dispensed.

In one embodiment, the forward nutrient-related sensor(s) 90A and/or the rearward nutrient-related sensor(s) 90B are positioned on the frame 12 of the planting implement. For example, as shown in FIG. 1, a forward nutrient-related sensor 90A and a rearward nutrient-related sensor 90B are positioned on each laterally extending wing of the frame 12 of the planting implement 10. In some embodiments, the forward nutrient-related sensor(s) 90A and/or a rearward nutrient-related sensor(s) 90B are alternatively, or additionally, positioned on one or more of the row units 18. For example, as shown in FIG. 2, the forward nutrient-related sensor 90A is positioned on the frame 34 of the row unit 18, adjacent a front end of the row unit 18 relative to the direction of travel 16 and the rearward nutrient-related sensor 90B is positioned on the frame 34, adjacent the rear end of the row unit 18 relative to the direction of travel 16. It should be appreciated that the data generated by the nutrient-related sensor(s) 90A, 90B on a first one of the row units 18 of the planting implement 10 may be used to control the first one of the row units 18 and one or more other row units 18 of the planting implement 10, such as directly laterally adjacent ones of the row units 18, other row units 18 of the same frame section, and/or the like to reduce the weight and/or costs associated with the sensor assembly.

However, it should be appreciated that the sensor(s) 90A, 90B may instead, or additionally, be positioned on an unmanned aerial vehicle (UAV) or drone (not shown). In such embodiment, the UAV or drone may be configured to perform a pre-planting pass across the field to collect the data indicative of the amount(s) of nutrient(s) in the field before the planting operation and/or to follow the planting implement 10 during the planting operation to generate data indicative of the updated amount(s) of the nutrient(s) in the field, after the planting operation.

The nutrient-related sensors 90A, 90B may be any suitable sensors or combination of sensors for detecting nutrient-related parameters including soil nutrient composition, soil moisture content, and/or the like. For instance, in some embodiments, the nutrient-related sensor(s) 90A, 90B may correspond to gamma ray sensor(s) configured to generate data indicative of the soil nutrient composition (e.g., potassium, thorium, uranium, and cesium within soil) and/or the soil moisture content, electromagnetic sensor(s) configured to generate data indicative of the soil nutrient composition (e.g., organic matter content and mineral composition) and the moisture content, electrochemical sensor(s) configured to generate data indicative of the soil nutrient composition (e.g., potassium, phosphorus, nitrogen, etc.), a capacitance sensor configured to generate data indicative of the soil moisture content, a ground-penetrating radar configured to generate data indicative of the soil moisture content, and/or any other suitable sensors. In some embodiments, the nutrient-related sensor(s) 90A, 90B may correspond to non-contact sensors. However, in other embodiments, the nutrient-related sensor(s) 90A, 90B may additionally, or alternatively, correspond to contact sensors.

It should be appreciated that the configuration of the row unit 18 described above and shown in FIG. 2 is provided only to place the present subject matter in an exemplary field of use. Thus, it should be appreciated that the present subject matter may be readily adaptable to any manner of seed planting unit configuration.

Figure 3:
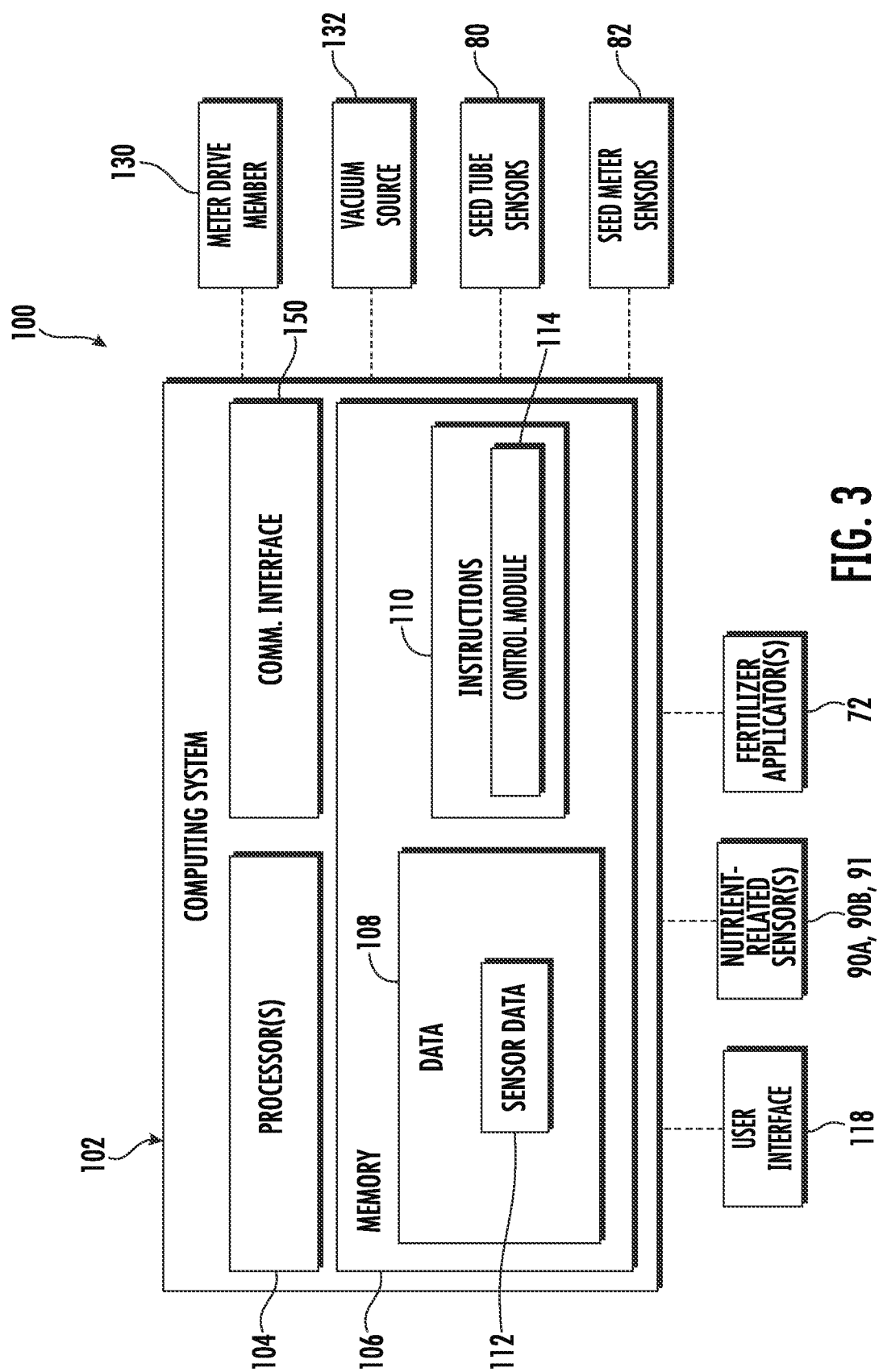
FIG. 3 illustrates a schematic view of a system for automatically controlling fertilizer application within a field during the performance of a planting operation with a planting implement in accordance with aspects of the present subject matter.

Referring now to FIG. 3, a schematic view of one embodiment of a system for automatically controlling fertilizer application within a field during the performance of a planting operation. In general, the system 100 will be described herein with reference to the planting implement 10, the row unit 18, and related components described above with reference to FIGS. 1 and 2. However, it should be appreciated that the disclosed system 100 may generally be utilized with any planter or seeder having any suitable implement configuration and/or with row units having any suitable row unit configuration.

In several embodiments, the system 100 may include a computing system 102 and various other components configured to be communicatively coupled to and/or controlled by the computing system 102, such as the fertilizer applicator(s) 72, a meter drive member 130 configured to rotationally drive the seed meter 50, a vacuum source 132 configured to apply a vacuum or negative pressure to the seed disk or seed transport member of the seed meter 50, and/or various sensors configured to monitor one or more operating parameters associated with the planting implement 10. For example, the computing system 102 may be communicatively coupled to the seed tube sensor(s) 80, the seed meter sensor(s) 82, and the nutrient-related sensor(s) 90A, 90B. In addition, the computing system 102 may be communicatively coupled to one or more additional sensors configured to generate data indicative of the frequency of the seeds being deposited within the furrow by each row unit, such as a seed tube sensor 80 and/or a seed meter sensor 82 provided in association with each row unit 18.

It should be appreciated that the computing system 102 may correspond to any suitable processor-based device(s), such as a computing device or any combination of computing devices. Thus, as shown in FIG. 3, the computing system 102 may generally include one or more processor(s) 104 and associated memory devices 106 configured to perform a variety of computer-implemented functions (e.g., performing the methods, steps, algorithms, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and any other programmable circuits. Additionally, the memory 106 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory 106 may generally be configured to store information accessible to the processor(s) 104, including data 108 that can be retrieved, manipulated, created and/or stored by the processor(s) 104 and instructions 110 that can be executed by the processor(s) 104.

In several embodiments, the data 108 may be stored in one or more databases. For example, the memory 106 may include a sensor database 112 for storing sensor data and/or other relevant data that may be used by the computing system 102 in accordance with aspects of the present subject matter. For instance, during operation of the planting implement, data from all or a portion of the sensors communicatively coupled to the computing system 102 may be stored (e.g., temporarily) within the sensor database 112 and subsequently used to determine one or more parameter values associated with the operation of the planting implement 10, including any or all data generated by the seed tube sensor(s) 80, the seed meter sensor(s) 82, and the nutrient-related sensor(s) 90A, 90B.

Moreover, in several embodiments, the instructions 110 stored within the memory 106 of the computing system 102 may be executed by the processor(s) 104 to implement a control module 114. In general, the control module 114 may be configured to control the operation of the meter drive members 130A, 130B and the vacuum sources 132 to control the dispensing of the seeds 41 into the furrow 39. For instance, the computing system 102 may monitor the position of the planter 10 relative to an associated planting prescription map and control the operation of the seed meter(s) 50A and the vacuum source(s) 132 to drop seeds 41 within a furrow 39 according to a desired population density, seed spacing, distance interval and/or the like prescribed by the prescription map.

The control module 114 may also be configured to control the operation of the fertilizer applicator(s) 72 of the row unit(s) 18 to selectively apply fertilizer to the field. For instance, the computing system 102 may be configured to control the operation of the fertilizer applicator(s) 72 to dispense the fertilizer only where needed in the field. For example, the control module 114 may be configured to determine an initial amount of one or more nutrients within the field based at least in part on the data received from the forward nutrient-related sensor(s) 90A indicative of one or more first nutrient-related parameters. Thereafter, the control module 114 may control the operation of the corresponding fertilizer applicator(s) 72 to apply the fertilizer based on the initial amount(s) of the nutrient(s) within the field. For instance, the control module 114 may compare the initial amount(s) of the nutrient(s) within the field based on the data generated by the forward nutrient-related sensor(s) 90A to one or more limits or thresholds corresponding to respective ones of the nutrient(s) and control the operation of the fertilizer applicator(s) 72 based at least in part on the comparison. The limit(s) may be predetermined or selected based at least in part on the soil type and/or seeds being planted.

If the initial amount(s) of one or more of the nutrients within the area of the field indicated by the data generated by the forward nutrient-related sensor(s) 90A is below the minimum limit or threshold(s) corresponding to the nutrient(s), the control module 114 may control the operation of the fertilizer applicator(s) 72 to apply fertilizer to increase the amount of nutrients in the indicated area of the field. More particularly, the control module 114 may control the operation of the fertilizer applicator(s) 72 to apply fertilizer based on the difference between the limit(s) and the corresponding initial amounts of nutrient(s) to increase the amount of nutrients within the indicated area of the field. For instance, the control module 114 may control the operation of the fertilizer applicator(s) 72 based on a relationship (e.g., an algorithm, a lookup table, etc.) correlating the difference between the limit(s) and the corresponding initial amounts of nutrient(s) to a recommended dispensing rate or quantity of fertilizer to be applied. The relationship may be based at least in part on the speed of the fertilizer pump, the pressure of the fertilizer system, the percentage of opening of a nozzle of the fertilizer applicator 72, the type of fertilizer, and/or the type of seed(s) to be planted. Similarly, if the initial amount(s) of one or more of the nutrients within the field is at or exceeds the maximum limit or threshold(s) corresponding to the nutrient(s), the control module 114 may control the operation of the fertilizer applicator(s) 72 according to the relationship to reduce or stop applying the fertilizer so as to not exceed, or not further exceed, the limits. It should be appreciated that the control module 114 may control the fertilizer applicator 72 to account for the difference between when a portion of the field is detected by the forward nutrient-related sensor 90A and when the fertilizer applicator 72 will dispense in the same portion of the field based on a speed of the planting implement and a distance between a field of view of the sensor 90A and a spray range of the fertilizer applicator 72 along the direction of travel 16.

In several embodiments, the control module 116 may further be configured to adjust the seed planting parameters (e.g., population density, seed spacing, distance interval and/or the like) when one or more of the prescribed seed planting parameters is not suitable for the actual nutrients within the field. In such case, the control module 116 may be configured to adjust the seed planting parameters to be more suitable. For example, if the initial nutrient(s) within the field is too high, the control module 116 may prevent leaching by increasing the population density, reducing seed spacing, reducing distance interval, and/or the like.

The control module 114 may additionally be configured to determine an updated amount of the one or more nutrients within the field after fertilizer has been applied based at least in part on the data received from the rearward nutrient-related sensor(s) 90B indicative of one or more second nutrient-related parameters. For instance, data from the sensor(s) 90B may be directly indicative of the nutrient(s) within the soil or may be indirectly indicative of the nutrient(s) within the soil, such as indicative of the moisture content of the soil which is relatable to the amount of nutrient(s) within the soil. It should be appreciated that the sensor(s) 90A, 90B may be the same type of sensor (e.g., soil nutrient sensors or soil moisture sensors) such that the data from the rearward nutrient-related sensor(s) 90B is indicative of the same nutrient-related parameters (e.g., soil nutrients and/or moisture) as the forward nutrient-related sensor(s) 90A. However, in other embodiments, the sensor(s) 90A, may be different sensors such that the data from the rearward nutrient-related sensor(s) 90B is indicative of the different nutrient-related parameters (e.g., moisture) from the nutrient-related parameters (e.g., soil nutrient composition) indicated by the data generated by the forward nutrient-related sensor(s) 90A. Additionally, in embodiments where both the sensors 90A, 90B are soil nutrient sensors, the sensor(s) 90B or one or more additional sensors 91 may be configured to additionally determine the soil moisture content within the field. In such embodiment, the data from the sensor(s) 90A, 90B and/or additional sensor(s) 91 may be used to determine the moisture content within the field, which may, in turn, be used to select or otherwise determine the limit(s) or threshold(s) corresponding to the nutrient(s). For instance, when there is a lower moisture content within the field, it may be beneficial to apply less fertilizer to the field, whereas, when there is a higher moisture content within the field, it may be beneficial to apply more fertilizer to the field.

Thereafter, the control module 114 may be configured to calibrate or adjust the operation of the fertilizer applicator(s) 72 based at least in part on the updated amounts of the nutrient(s) within the field. For instance, the control module 114 may compare the updated amounts of the nutrient(s) within the field to the limit(s) corresponding to respective ones of the nutrient(s) and control the operation of the fertilizer applicator(s) 72 based at least in part on the comparison of the updated amounts to the limit(s). For instance, if the updated amount(s) of one or more of the nutrients within the field remains below a minimum limit(s) corresponding to the nutrient(s), the control module 114 may determine that the fertilizer applicator(s) 72 did not apply enough fertilizer for the corresponding initial amount(s) of nutrient(s). Then, the control module 114 may calibrate or adjust control of the operation of the fertilizer applicator(s) 72 to increase the amount or dispensing rate of fertilizer to be applied to the field for subsequent areas in the field with a similar difference between the initial amount(s) of nutrients and the minimum limit(s). In some instances, the control module 114 may update the relationship, correlating the difference between the limit(s) and the initial amount(s) of nutrient(s) to a recommended dispensing rate or quantity of fertilizer, to increase the quantity of fertilizer recommended by the relationship to be applied based at least in part on the difference between the limit(s) and the updated amounts of nutrient(s).

Conversely, if the updated amount(s) of one or more of the nutrients within the field after applying fertilizer is above the maximum limit(s) corresponding to the nutrient(s), the control module 114 may determine that the fertilizer applicator(s) 72 is applying too much fertilizer. Then, the control module 114 may calibrate or adjust control of the operation of the fertilizer applicator(s) 72 to reduce the amount or dispensing rate of fertilizer to be applied to the field for subsequent areas in the field with a similar difference between the initial amount(s) of nutrient(s) within the field and the maximum limit(s). In some instances, the control module 114 may update the relationship, correlating the difference between the limit(s) and the initial amount(s) of nutrient(s) to a recommended quantity of fertilizer, to decrease the quantity of fertilizer recommended by the relationship based at least in part on the difference between the limit(s) and the updated amounts of nutrient(s).

Additionally, the control module 114 may additionally be configured to monitor the status of the fertilizer applicator(s) 72. For instance, the control module 114 may additionally compare the updated amount(s) of nutrient(s) within the field to the initial amount(s) of nutrient(s) within the field. If the updated amount(s) are essentially the same as or equal to the initial amount(s) of nutrient(s) within the field when the updated amount(s) should be higher than the initial amount(s), such as when the initial amount(s) was below the minimum limit(s), the control module 114 may determine that the corresponding fertilizer applicator(s) 72 is impaired, for instance, the fertilizer applicator(s) 72 may be plugged or otherwise not functioning properly (e.g., the associated pump and/or valve is not operating properly, the fertilizer tank is empty, and/or the like). In some instances, the control module 114 may further be configured to control an operation of a user interface 118 to indicate to an operator which fertilizer applicator(s) 72 is impaired based on the comparison of the updated amount(s) of nutrient(s) within the field to the initial amount(s) of nutrient(s) within the field.

Moreover, as shown in FIG. 3, the computing system 102 may also include a communications interface 150 to provide a means for the computing system 102 to communicate with any of the various other system components described herein. For instance, one or more communicative links or interfaces (e.g., one or more data buses) may be provided between the communications interface 150 and the fertilizer applicator(s) 72, the user interface(s) 118, the meter drive member(s) 130, and the vacuum source(s) 132 to allow the computing system 102 to transmit control signals for controlling the operation of such components. Similarly, one or more communicative links or interfaces (e.g., one or more data buses) may be provided between the communications interface 150 and the various sensors 80, 82, 90A, 90B to allow the associated sensor data to be transmitted to the computing system 102.

It should be appreciated that, in general, the computing system 102 may include any suitable computing device(s) configured to function as described herein. In several embodiments, the computing system 102 may form part of an active planting system configured to perform a planting operation, such as by including a vehicle controller of a work vehicle configured to tow an associated planting implement 10 and/or an associated implement controller of the planting implement 10.

Figure 4:
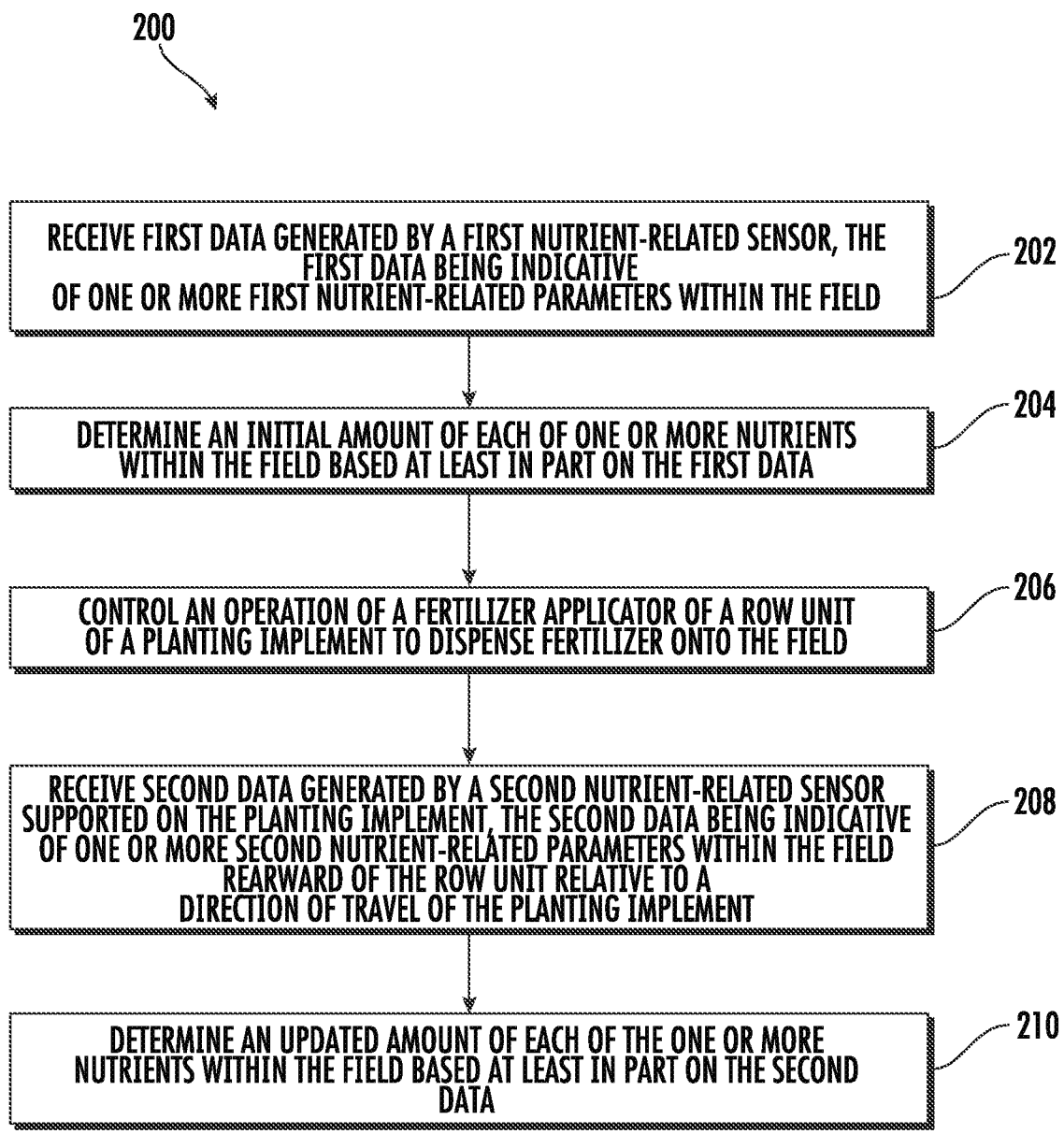
FIG. 4 illustrates a flow diagram of one embodiment of a method for automatically controlling fertilizer application within a field during the performance of a planting operation with a planting implement in accordance with aspects of the present subject matter.

Referring now to FIG. 4, a flow diagram of one embodiment of a method 200 for automatically controlling fertilizer application within a field during the performance of a planting operation with a planting implement is illustrated in accordance with aspects of the present subject matter. In general, the method 200 will be described herein with reference to the planting implement 10, row unit 18, and system 100 described above with reference to FIGS. 1-3. However, it should be appreciated by those of ordinary skill in the art that the disclosed method 200 may generally be utilized to monitor seed placement in associated with any planting implement having any suitable implement configuration, any row unit having any suitable row unit configuration, and/or any system having any suitable system configuration. In addition, although FIG. 4 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 4, at (202), the method 200 may include receiving first data generated by a first nutrient-related sensor, the first data being indicative of one or more first nutrient-related parameters within the field. For instance, as discussed above, the computing system 102 may receive the data generated by the forward nutrient-related sensor(s) 90A supported on the planting implement 10, where the data generated by the forward nutrient-related sensor(s) 90A is indicative of one or more first nutrient-related parameters within the field, forward of one or more of the row units 18 of the planting implement 10 relative to the forward direction of travel 16 of the planting implement 10.

Further, at (204), the method 200 may include determining an initial amount of each of one or more nutrients within the field based at least in part on the first data. For example, as described above, the computing system 102 may determine an initial amount of each of the one or more nutrients within the field based at least in part on the data generated by the forward nutrient-related sensor(s) 90A.

Furthermore, at (206), the method 200 may include controlling an operation of a fertilizer applicator of a row unit of a planting implement to dispense fertilizer onto the field. For instance, as described above, the computing system 102 may control an operation of the fertilizer applicator(s) 72 of the row unit(s) 18 to dispense fertilizer onto the field, such as to dispense fertilizer based on the initial amount(s) of the nutrient(s) within the field. For example, the computing system 102 may control an operation of the fertilizer applicator(s) 72 of the row unit(s) 18 to dispense fertilizer onto the field when the initial amount(s) of the nutrient(s) is below a minimum limit(s) and to not dispense fertilizer onto the field when the initial amount(s) of the nutrient(s) is equal to or exceeds a maximum limit(s).

Moreover, at (208), the method 200 may include receiving second data generated by a second nutrient-related sensor supported on the planting implement, the second data being indicative of one or more second nutrient-related parameters within the field, rearward of the row unit relative to a direction of travel of the planting implement. For example, as described above, the computing system 102 may receive data generated by the rearward nutrient-related sensor(s) 90B supported on the planting implement 10, the data generated by the rearward nutrient-related sensor(s) 90B being indicative of one or more second nutrient-related parameters within the field, rearward of the row unit(s) 18 relative to the direction of travel 16 of the planting implement 10.

Additionally, at (210), the method 200 may include determining an updated amount of each of the one or more nutrients within the field based at least in part on the second data. For instance, as indicated above, the computing system 102 may determine an updated amount of the nutrient(s) within the field based at least in part on the data generated by the rearward nutrient-related sensor(s) 90B.

It is to be understood that the steps of the method 200 are performed by the computing system 100 upon loading and executing software code or instructions which are tangibly stored on a tangible computer readable medium, such as on a magnetic medium, e.g., a computer hard drive, an optical medium, e.g., an optical disk, solid-state memory, e.g., flash memory, or other storage media known in the art. Thus, any of the functionality performed by the computing system 100 described herein, such as the method 200, is implemented in software code or instructions which are tangibly stored on a tangible computer readable medium. The computing system 100 loads the software code or instructions via a direct interface with the computer readable medium or via a wired and/or wireless network. Upon loading and executing such software code or instructions by the computing system 100, the computing system 100 may perform any of the functionality of the computing system 100 described herein, including any steps of the method 200 described herein.

The term "software code" or "code" used herein refers to any instructions or set of instructions that influence the operation of a computer or computing system. They may exist in a computer-executable form, such as machine code, which is the set of instructions and data directly executed by a computer's central processing unit or by a computing system, a human-understandable form, such as source code, which may be compiled in order to be executed by a computer's central processing unit or by a computing system, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a computing system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for automatically controlling fertilizer application within a field during the performance of a planting operation, the system comprising:
   a row unit of a planting implement, the row unit being configured to deposit seeds within soil, the row unit including:
   a furrow opening assembly configured to create a furrow in the soil for depositing seeds within a field; and
   a fertilizer applicator configured to selectively dispense fertilizer onto the field;
   a first nutrient-related sensor configured to generate first data indicative of one or more first nutrient-related parameters within the field;
   a second nutrient-related sensor supported on the planting implement, the second nutrient-related sensor being configured to generate second data indicative of one or more second nutrient-related parameters within the field, rearward of the row unit relative to a direction of travel of the planting implement; and
   a computing system communicatively coupled to the fertilizer applicator, the computing system being configured to:
   receive the first data generated by the first nutrient-related sensor;
   determine an initial amount of each of one or more nutrients within the field based at least in part on the first data;
   control an operation of the fertilizer applicator to dispense the fertilizer onto the field;
   receive the second data generated by the second nutrient-related sensor; and
   determine an updated amount of each of the one or more nutrients within the field based at least in part on the second data.

2. The system of claim 1, wherein the computing system is configured to control the operation of the fertilizer applicator to dispense the fertilizer on to the field based at least in part on a comparison of the initial amounts of the one or more nutrients within the field to one or more limits corresponding to respective ones of the one or more nutrients.

3. The system of claim 2, wherein the computing system is further configured to adjust the operation of the fertilizer applicator based at least in part on a comparison of the updated amounts of the one or more nutrients within the field to the one or more limits.

4. The system of claim 1, wherein the computing system is further configured to determine that the fertilizer applicator is impaired when the updated amounts of the one or more nutrients is equal to the initial amounts of the one or more nutrients.

5. The system of claim 1, wherein each of the first nutrient-related sensor and the second nutrient-related sensor is a soil nutrient sensor, the one or more second nutrient-related parameters being the same parameters as the one or more first nutrient-related parameters.

6. The system of claim 5, further comprising a soil-moisture sensor configured to generate data indicative of a moisture content within the field,
   wherein the computing system is configured to determine the moisture content within the field based on the data from the soil-moisture sensor, and
   wherein the computing system is configured to control the operation of the fertilizer applicator to dispense the fertilizer on to the field based at least in part on a comparison of the initial amounts of the one or more nutrients within the field to one or more limits corresponding to respective ones of the one or more nutrients and the moisture content within the field.

7. The system of claim 1, wherein each of the first nutrient-related sensor and the second nutrient-related sensor is a soil moisture sensor, the one or more second nutrient-related parameters being the same parameters as the one or more first nutrient-related parameters.

8. The system of claim 1, wherein the row unit is one of a plurality of row units, the computing system being configured to control an operation of a fertilizer applicator of one or more other row units of the plurality of row units based at least in part on the first and second data received from the first and second nutrient-related sensors.

9. A method for automatically controlling fertilizer application within a field during the performance of a planting operation by a planting implement, the planting implement comprising a row unit having a furrow opening assembly configured to create a furrow in soil for depositing seeds, and the row unit having a fertilizer applicator configured to selectively dispense fertilizer onto the field, the method comprising:
  receiving, with a computing system, first data generated by a first nutrient-related sensor, the first data being indicative of one or more first nutrient-related parameters within the field;
  determining, with the computing system, an initial amount of each of one or more nutrients within the field based at least in part on the first data;
  controlling, with the computing system, an operation of the fertilizer applicator to dispense the fertilizer onto the field;
  receiving, with the computing system, second data generated by a second nutrient-related sensor supported on the planting implement, the second data being indicative of one or more second nutrient-related parameters within the field, rearward of the row unit relative to a direction of travel of the planting implement; and
  determining, with the computing system, an updated amount of each of the one or more nutrients within the field based at least in part on the second data.

10. The method of claim 9, wherein controlling the operation of the fertilizer applicator to dispense the fertilizer onto the field comprises controlling the operation of the fertilizer applicator to dispense the fertilizer onto the field based at least in part on a comparison of the initial amounts of the one or more nutrients within the field to one or more limits corresponding to respective ones of the one or more nutrients.

11. The method of claim 10, further comprising adjusting the operation of the fertilizer applicator based at least in part on a comparison of the updated amounts of the one or more nutrients within the field to the one or more limits.

12. The method of claim 11, further comprising adjusting the operation of the fertilizer applicator to decrease a dispensing rate of the fertilizer for subsequent areas of the field when the updated amount of at least one of the one or more nutrients within the field exceeds a maximum limit of the one or more limits corresponding to the at least one of the one or more nutrients.

13. The method of claim 11, further comprising adjusting the operation of the fertilizer applicator to increase a dispensing rate of the fertilizer for subsequent areas of the field when the updated amount of at least one of the one or more nutrients within the field remains below a minimum limit of the one or more limits corresponding to the at least one of the one or more nutrients.

14. The method of claim 9, further comprising determining that the fertilizer applicator is impaired when the updated amounts of the one or more nutrients is equal to the initial amounts of the one or more nutrients.

15. The method of claim 14, further comprising controlling an operation of a user interface to indicate to an operator that the fertilizer applicator is impaired.

16. The method of claim 9, wherein each of the first nutrient-related sensor and the second nutrient-related sensor is a soil nutrient sensor, the one or more second nutrient-related parameters being the same parameters as the one or more first nutrient-related parameters.

17. The method of claim 9, wherein the first nutrient-related sensor is a soil nutrient sensor and the second nutrient-related sensor is a soil moisture sensor, the one or more first nutrient-related parameters comprising one or more soil nutrients, and the one or more second nutrient-related parameters comprising a moisture content of the field.

18. The method of claim 9, further comprising controlling an operation of a fertilizer applicator of one or more other row units of the planting implement based at least in part on the first and second data received from the first and second nutrient-related sensors.

19. A system for automatically controlling fertilizer application within a field during the performance of a planting operation, the system comprising:
  a row unit of a planting implement, the row unit being configured to deposit seeds within soil, the row unit including:
    a furrow opening assembly configured to create a furrow in the soil for depositing seeds within a field; and
    a fertilizer applicator configured to selectively dispense fertilizer onto the field;
  a first nutrient-related sensor configured to generate first data indicative of one or more first nutrient-related parameters within the field;
  a second nutrient-related sensor supported on the planting implement, the second nutrient-related sensor being configured to generate second data indicative of one or more second nutrient-related parameters within the field, rearward of the row unit relative to a direction of travel of the planting implement; and
  a computing system communicatively coupled to the fertilizer applicator, the computing system being configured to:
    receive the first data generated by the first nutrient-related sensor;
    determine an initial amount of each of one or more nutrients within the field based at least in part on the first data;
    control an operation of the fertilizer applicator to dispense the fertilizer onto the field based at least in part on a comparison of the initial amounts of the one or more nutrients within the field to one or more limits corresponding to respective ones of the one or more nutrients, the one or more limits including a maximum limit corresponding to each of the one or more nutrients and a minimum limit corresponding to each of the one or more nutrients;
    receive the second data generated by the second nutrient-related sensor;
    determine an updated amount of each of the one or more nutrients within the field based at least in part on the second data; and
    control the operation of the fertilizer applicator to at least one of:
      decrease a dispensing rate of the fertilizer for subsequent areas of the field when the updated amount of at least one of the one or more nutrients within the field exceeds the maximum limit corresponding to the at least one of the one or more nutrients; or increase the dispensing rate of the fertilizer for the subsequent areas of the field when the updated amount of at least one of the one or more nutrients within the field remains below the minimum limit corresponding to the at least one of the one or more nutrients.

\* \* \* \* \*